United States Patent [19]

Westermann et al.

[11] Patent Number: 5,391,778

[45] Date of Patent: Feb. 21, 1995

[54] 2-IODO-3-KETO-$\Delta^4$ STEROIDS, PROCESS FOR THEIR PRODUCTION, AS WELL AS THEIR FURTHER PROCESSING

[75] Inventors: Jürgen Westermann; Klaus Nickisch; Michael Harre; Ralph Rohde, all of Berlin, Germany

[73] Assignee: Schering Aktiengesellschaft, Berlin and Bergkamen, Germany

[21] Appl. No.: 960,385

[22] PCT Filed: May 8, 1991

[86] PCT No.: PCT/DE91/00386

§ 371 Date: Jan. 11, 1993

§ 102(e) Date: Jan. 11, 1993

[87] PCT Pub. No.: WO91/17175

PCT Pub. Date: Nov. 14, 1991

[30] Foreign Application Priority Data

May 9, 1990 [DE] Germany ............... 4015247

[51] Int. Cl.[6] ............... C07C 45/65
[52] U.S. Cl. ............... 552/634; 552/625; 552/643
[58] Field of Search ............... 552/646, 625, 630, 634, 552/643

[56] References Cited

U.S. PATENT DOCUMENTS

| | | | |
|---|---|---|---|
| 3,546,259 | 12/1970 | Boswell, Jr. et al. | 260/397.4 |
| 3,775,404 | 11/1973 | Buzby, Jr. et al. | 260/239.55 |
| 4,311,646 | 1/1982 | Nitta et al. | 260/397.4 |
| 4,871,482 | 10/1989 | Nickisch et al. | 260/397.3 |

OTHER PUBLICATIONS

Brodie et al., "Steroids", 6:6, Dec. 1965, pp. 659–674.
Shaw et al., "Journal of Medicinal Chemistry", 7:4, Jul. 1964, pp. 555–560.
Berkoz et al., "Journal of Organic Chemistry", 28:8, Aug. 1963, pp. 1976–1982.

Primary Examiner—José G. Dees
Assistant Examiner—B. Frazier
Attorney, Agent, or Firm—Millen, White, Zelano & Branigan

[57] ABSTRACT

The new intermediate products of general formula I

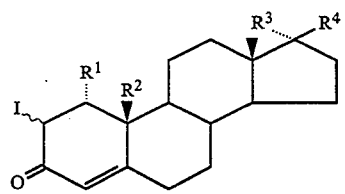

in which
$R^1$ stands for a hydrogen atom or a straight-chain or branched alkyl group with 1 to 4 carbon atoms,
$R^2$ stands for a hydrogen atom or a methyl group,
$R^3$ stands for a hydrogen atom,
$R^4$ stands for an acyloxy group with 1 to 4 carbon atoms in the acyl radical or
$R^3$ and $R^4$ together stand for a keto-oxygen atom, are suitable in an excellent way for introducing a $\Delta^1$ double bond in the steroid skelton with the simultaneous presence of a $\Delta^4$ double bond, as well as a saturated carbonyl group, by clevage of hydrogen iodide with a base in an amidic solvent at elevated temperature. If $R^2$ stands for a hydrogen atom, the A-ring is aromatized after the hydrogen iodide cleavage. For the production of a new intermediate products, special iodization processes, which partially also allow a stereoselective control of the iodization, are used.

9 Claims, No Drawings

2-IODO-3-KETO-$\Delta^4$ STEROIDS, PROCESS FOR THEIR PRODUCTION, AS WELL AS THEIR FURTHER PROCESSING This invention relates to new intermediate products of general formula I

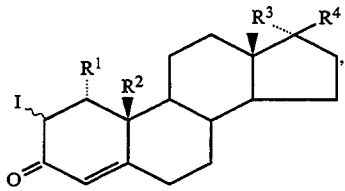

in which
- $R^1$ stands for a hydrogen atom or a straight-chain or branched alkyl group with 1 to 4 carbon atoms,
- $R^2$ stands for a hydrogen atom or a methyl group,
- $R^3$ stands for a hydrogen atom,
- $R^4$ stands for an acyloxy group with 1 to 4 carbon atoms in the acyl radical or else
- $R^3$ and $R^4$ together stand for a keto-oxygen atom.

A hydrogen atom or a methyl group is preferred for $R^1$.

As acyloxy group $R^4$, first of all the acetoxy group is suitable.

This invention especially relates to the following compounds:
2β-Iodo-1α-methylandrost-4-ene-3,17-dione;
2⊕-iodo-1α-methylandrost-4-ene-3,17-dione;
2-iodo-androst-4-ene-3,17-dione;
17β-acetoxy-2-iodo-1α-methyl-androst-4-en-3-one;
2-iodo-19-nor-androst-4-ene-3,17-dione;
17β-acetoxy-2-iodo-androst-4-en-3-one.

The intermediate products of general formula I are suitable in an excellent way for introducing a $\Delta^1$ double bond in the steroid skeleton with the simultaneous presence of a $\Delta^4$ double bond as well as saturated carbonyl groups.

Reaction of a compound of general formula I with a base in an amidic solvent at elevated temperature with cleavage of hydrogen iodide results in a compound of general formula II

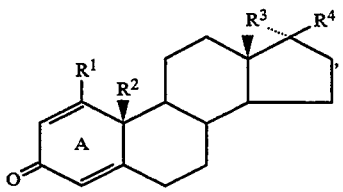

in which $R^1$, $R^2$, $R^3$ and $R^4$ have the meaning indicated in formula I.

If $R^2$ stands for a hydrogen atom, after the hydrogen iodide cleavage, the A-ring aromatizes with the formation of a compound of general formula II'

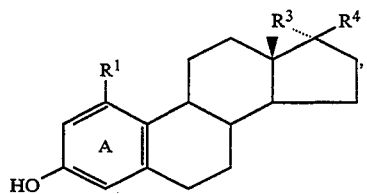

This invention further relates to a process for the production of new intermediate products of general formula I.

In this connection, either a compound of general formula III

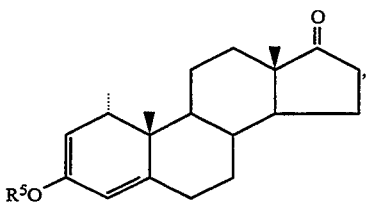

in which
$R^5$ means an acyl or trialkylsilyl group with up to 10 carbon atoms in the group (EP-A 0290378; DE-A 3 715 869), is reacted with N-iodosuccinimide, optionally generated in situ, in a solvent, for example in an alcohol such as methanol, ethanol, propanol or the like to the compound of general formula Ia

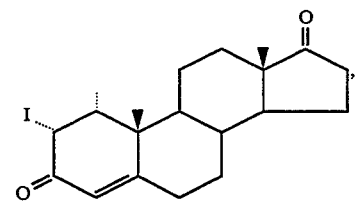

or with iodomonochloride or iodomonobromide in an aprotic solvent in the presence of a base or with elementary iodine in acetic acid by adding a base to the compound of formula Ib

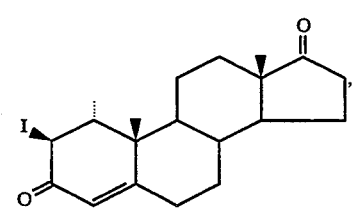

or a compound of general formula IV

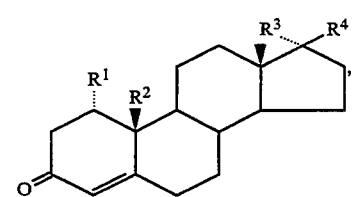

in which $R^1$, $R^2$, $R^3$ and $R^4$ have the meaning indicated in formula I,
is reacted with elementary iodine, iodomonochloride or iodomonobromide, N-iodosuccinimide or an N-iodamide, such as 1,3-diiodo-5,5-dimethylhydantoin or another N-iodimide in the presence of an equimolar amount of a copper compound in acetic acid or in an inert solvent, e.g., in an ether such as THF, by adding a catalytic amount of acetic acid or another $C_1$–$C_3$ carboxylic acid to a compound of general formula Ic

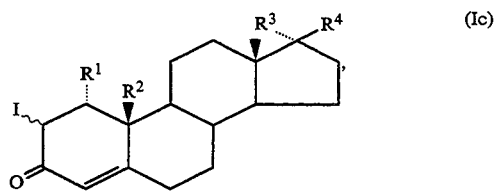

By selecting the reaction conditions, the stereochemistry of the iodization reaction can thus be controlled, namely so that either the 2α-form Ia, the 2β-form Ib or a 2α/2β mixture can be produced. Regioselective iodizations on 3,17-diketo steroids are new, as is the already mentioned $\Delta^1$-introduction on 1-alkyl-substituted steroids by hydrogen iodide cleavage. The reaction in the allyl position frequently occurring in brominations (see the literature indicated on p. 6: C. Djerassi; A. Corbellini) is not observed in the iodization.

Similar compounds with 2-iodo-3-keto-$\Delta^4$ structure (without 1-alkyl substituent) are already known, but have been produced in low yield from the corresponding bromine compound by halogen exchange with sodium iodide [J. Am. Chem. Soc. 72, 4077, (1962)].

Advantageous embodiments of the process for the production of compounds of general formula I follow from subclaims 4 to 10.

The reaction of the compounds of general formula III with N-iodosuccinimide is preferably performed in an alcohol such as methanol, ethanol, propanol or 2-propanol. The reaction takes place with N-iodosuccinimide generated in situ, best of all in acetone or methanol.

As solvent for the iodization of the compounds of general formula III or IV with iodomonochloride or iodomonobromide, ethers such as tetrahydrofuran or ketones such as, for example, acetone or methyl isobutyl ketone, have proven especially suitable.

The iodization of compounds of general formula III with elementary iodine is performed preferably of all in glacial acetic acid as solvent.

As a base for iodization with iodomonochloride, iodomonobromide or with elementary iodine, especially a carboxylic acid salt such as sodium acetate or the like or an amine such as, for example, triethylamine or pyridine is considered.

Copper(II) oxide, acetate, chloride, bromide, iodide or copper(I) chloride are the preferred copper compounds in whose presence the iodization of the compounds of general formula IV is performed.

A well known representative of a compound of general formula II is 1-methyl-androsta-1,4-diene-3,17-dione (Atamestan); Atamestan is a very effective inhibitor of the estrogen biosynthesis (DE-A 33 22 285). 1-Methyl-androsta-1,4-diene-3,17-dione previously was produced by oxidation of 17β-hydroxy-1-methyl-androsta-1,4-dien-3-one or by microbiological dehydration of 1-methyl-5α-androst-1-ene-3,17-dione (DE-A 35 12 328). The production of these two compounds takes place by multistage syntheses (5 reaction steps) and in low yields.

In this connection, the introduction of the $\Delta^1$ double bond on asteroid with a $\Delta^4$ double bond, especially in the presence of a 1α-methyl group, represents a problem.

No suitable process is known to get from a 1α-methyl-4-androstene-3,17-dione directly to 1-methyl-androsta-1,4-diene-3,17-dione.

The introduction of a $\Delta^1$ double bond in a 3-keto-1-methyl-$\Delta^4$ steroid (e.g., in 1α-methyl testosterone) with 2,3-dichloro-5,6-dicyano-benzoquinone (DDQ) yields $\Delta^{1,4}$ and $\Delta^{4,6}$ product in the ratio 1:2 and is therefore unsuitable as an economical process (A. B. Turner, H. J. Ringold, J. Chem. Soc. (C), 1967., 1720).

In Synthesis 1981, 312, it is described to iodize compounds with only one keto group in the 2-position. The listed examples show that saturated and unsaturated ketones (α,β-unsaturated carbonyl compound) react equally quickly and do not differ in reactivity.

It is all the more surprising that the iodization of the 3,17-diketones of general formula IV according to the invention takes place regioselectively.

The direct bromination of, e.g., 3-keto-$\Delta^4$ steroids is not suitable to produce 2-bromo-3-keto-$\Delta^4$ steroids. Thus, the bromination of androst-4-ene-3,17-dione yields 2,6-dibromo-androst-4-ene-3,17-dione as product. In this case, a nonselective bromination takes place in the 2- and 6-positions on the steroid (C. Djerassi, J. Am. Chem. Soc., 72, 4534 (1950); A. Corbellini, Farmaco Ed. Sci., 19, 913 (1964)).

A simpler process for the production of 1-methyl-androsta-1,4-diene-3,17-dione with a shorter synthesis method can be seen from EP-A 0290 378. Androsta-1,4-diene-3,17-dione [J. Am. Chem. Soc., 79, 3920 (1957), Tetrahedron 4, 201 (1958)] is converted by reaction with a reagent yielding methyl anions in the meaning of a Michael Addition and by subsequent trapping of the formed enolates to a compound of formula III

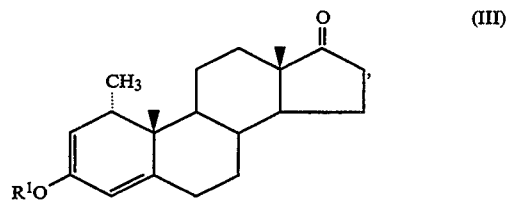

in which
$R^1$ means an alkyl radical with 1–3 carbon atoms or an acyl or trialkylsilyl group with up to 10 carbon atoms in the group,
the latter is converted by bromination to a 2-bromo steroid of formula

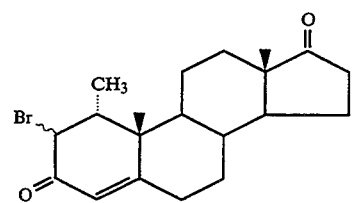

and the 2-bromo steroid is further processed by dehydrobromination to the end compound.

The iodization of a compound of formula III according to this invention takes place more cleanly and with better yield than the bromination described in EP-A 0290 378. This allows a simpler handling of the reaction and working up of the iodides, e.g., by crystallization.

Also, the reaction of a compound of general formula I with a base for cleavage of hydrogen iodide takes place more cleanly than the hydrobromic acid cleavage. Surprisingly, by using an iodine compound of formula I, the main secondary reaction, namely the formation of the $\Delta^{4,6}$ structure, can be repressed (<1%).

But this new process is suitable not only for the production of 1-methyl-androsta-1,4-diene-3,17-dione, but is also generally useful for introducing a $\Delta^1$ double bond on the steroid in the simultaneous presence of a $\Delta^4$ double bond and saturated carbonyl groups.

This invention therefore also relates to such a process for introducing a $\Delta^1$ double bond.

The cleavage of hydrogen iodide from a compound of general formula I according to this invention is preferably performed with a base such as magnesium oxide, lithium, sodium, potassium carbonate or the like. As solvent, preferably basic solvents such as dimethylformamide or N-methyl-pyrrolidone can be used. The temperature in the dehydrohalogenation is to be between 100° and 150° C.

If the compound of general formula I is a 19-nor steroid, i.e., $R^2=H$, the new process for aromatizing the A-ring of the steroid skeleton can be used.

M. I. Al-Hassan recently described an alternative method for aromatizing cyclohexenone systems (Synth. Commun. 19, (1989) 453; as well as other methods cited there). Deprotonation of 19-nor-testosterone, reaction with problematical phenylselenyl chloride and oxidation with peracid yields, after working up, β-estradiol in 40% yield.

The new process for introducing a $\Delta^1$ double bond yields the corresponding end products in high total yield. Starting from 1α-methyl-androst-4-ene-3,17-dione, only 2 reaction steps are necessary.

The following embodiments are used for a more detailed explanation of the invention.

EXAMPLE 1

2β-Iodine-1α-methylandrost-4-ene-3,17-dione 17.1 g (50 mmol) of 3-acetoxy1α-methyl-androsta-2,4-dien-17-one (DE-A 3715869) is dissolved in 235 ml of acetone and mixed with 8.2 g (100 mmol) of anhydrous sodium acetate. After cooling to −10° C., 9.75 g (60 mmol) of iodine chloride is added under nitrogen atmosphere. It is stirred for 30 more minutes at −10° C. The reaction solution is added with stirring in 1 l of ice water mixed with 2 g of sodium thiosulfate. The solid is suctioned off and rewashed with water. After drying of the substance, 21 g of the title compound (99% of theory) of melting point 119° C. is obtained.

EXAMPLE 2

1-Methylandrosta-1,4-diene-3,17-dione 2.13 g (5 mmol) of 2β-iodo-1α-methylandrost-4-ene-3,17-dione of example 1 is introduced in a suspension of 0.73 g (10 mmol) of lithium carbonate in 10 ml of dimethylformamide preheated to 130° C. and stirred for 1.5 hours at this temperature. After cooling, the reaction solution is added to 30 ml of water, extracted with ethyl acetate and after drying on sodium sulfate, concentrated by evaporation. The crude product is chromatographed on silica gel with ethyl acetate/hexane as mobile solvent. After recrystallization from ethyl acetate, 1.1 g of 1-methylandrosta-1,4-diene-3,17-dione (74% of theory) of melting point 169° C. is obtained.

EXAMPLE 3

2α-Iodo-1α-methylandrost-4-ene-3,17-dione 3.42 g (10 mmol) of 3-acetoxy-1α-methyl-androsta-2,4-dien-17-one (DE-A 3715869) is dissolved in 40 ml of absolute methanol. 2.25 g (10 mmol) of N-iodosuccinimide is added under nitrogen atmosphere and it is stirred for 1 hour at room temperature. The reaction mixture is added with stirring in 70 ml of ice water and the product is extracted with ethyl acetate. The organic phase is washed with 50 ml of water and dried on sodium sulfate. After chromatography of the crude product on silica gel with ethyl acetate/hexane as mobile solvent, 2.36 g (55.4% of theory) of 2α-iodo-1α-methylandrost-4-ene-3,17-dione is obtained as solid.

EXAMPLE 4

1-Methylandrosta-1,4-diene-3,17-dione 147.78 mg (2 mmol) of lithium carbonate is heated to 130° C. in 3 ml of N-methyl-pyrrolidone under nitrogen atmosphere. 426 mg (1 mmol) of 2α-iodo-1α-methylandrost-4-ene-3,17-dione of example 3 is added to this preheated solution. The solution is stirred for another 2 hours at this temperature. After cooling to room temperature, the solution is added in 20 ml of ice water and the product is extracted with ethyl acetate. After evaporation of the solvent, the crude product is purified with ethyl acetate/hexane as mobile solvent by chromatography on silica gel. Concentration by evaporation of the fractions and recrystallization from ethyl acetate yields 178 mg (60% of theory) of 1-methylandrosta-1,4-diene-3,17-dione of melting point 169° C.

EXAMPLE 5

2β-Iodo-1α-methylandrost-4-ene-3,17-dione 68.95 g of 88.8% (0.179 mol) 3-acetoxy-1α-methyl-androsta-2,4-dien-17-one (DE-A 3715869) is dissolved in 800 ml of acetone, mixed with 32.9 g (0.4 mol) of anhydrous sodium acetate and cooled with stirring to −10° C. Then, 29 g (0.179 mol) of iodine chloride (iodine monochloride) is added under nitrogen atmosphere at −10° C. and it is stirred for another 30 minutes. Then, it is added to 6 l of ice water mixed with 6.65 g of sodium thiosulfate, the product is extracted with ethyl acetate, the organic phase is dried on sodium sulfate, filtered and concentrated by evaporation up to 200 ml. After standing overnight, the precipitated solid is suctioned off and dried. 49 g (64% of theory) of product is obtained. After chromatography of the mother liquor on silica gel with ethyl acetate/hexane as mobile solvent, another 10 g (13% of theory) of the title compound is obtained. The total yield is 59 g (77% of theory) of 2β-iodo-1α-methylandrost-4-ene-3,17-dione.

EXAMPLE 6

1-Methylandrosta-1,4-diene-3,17-dione 19.40 g (0.262 mol) of lithium carbonate is suspended in 280 ml of absolute dimethylformamide and heated under nitrogen atmosphere to 130° C. At this temperature, 56 g (0.131 mol) of 2β-iodo-1α-methylandrost- 4-ene-3,17-dione of example 5 is added in portions. The solution is stirred for another hour at this temperature under nitrogen atmosphere. Then, dimethyl formamide is distilled off on a rotary evaporator under reduced pressure. The residue is taken up in 400 ml of ethyl acetate, mixed with 400 ml of water, the water phase is extracted again after phase separation with 2×200 ml of ethyl acetate and the ethyl acetate phase is washed with 150 ml of 10% sodium thiosulfate solution and dried on sodium sulfate. After cooling, 23.5g of crystals is obtained from the ethyl acetate solution concentrated by evaporation to 80 ml. The mother liquor is chromatographed on silica gel with hexane/ethyl acetate as mobile solvent. The chromatographically purified product is combined with the crystallizate and recrystallized from ethyl acetate. After filtering off and drying, 31.3 g of 1-methylandrosta-1,4-diene-3,17-dione (80.2% of theory) is obtained as colorless crystals of melting point 170° C. The purity of the thus obtained substance is 99.85% according to HPLC.

EXAMPLE 7

2-Iodo-1α-methyl-androst-4-ene-3,17-dione 10.3 g (40 mmol) of iodine is added to 10 g (33 mmol) of 1α-methyl-androst-4-ene-3,17-dione and 7.33 g (40 mmol) of CuO in 300 ml of glacial acetic acid with stirring at room temperature. It is stirred under nitrogen atmosphere for 24 hours at 60° C. Under reduced pressure, acetic acid is distilled off. The residue is added in 600 ml of water, the product is extracted 3 times with 200 ml of ethyl acetate each, the combined ethyl acetate phases are washed neutral with sodium thiosulfate solution, then with saturated sodium carbonate solution and dried on sodium sulfate. After concentration by evaporation of the solution and drying of the substance at 0.8 torr, 15.0 g (106% of theory) of 2-iodo-1α-methyl-androst-4-ene-3,17-dione is obtained as crude product.

EXAMPLE 8

1-Methyl-androsta-1,4-diene-3,17-dione 14.9 g of 2-iodo-1α-methyl-androst-4-ene-3,17-dione crude product of example 7 and 4.73 g (64 mmol) of anhydrous lithium carbonate are stirred in 95 ml of N-methyl-pyrrolidone for 1 hour at 130° C. under nitrogen atmosphere. After cooling of the reaction solution it is added to 0.6 l of water and the product is extracted 3 times with 450 ml of ethyl acetate. The combined ethyl acetate phases are dried on sodium sulfate and then concentrated by evaporation. The residue is chromatographed on silica gel with ethyl acetate/hexane as mobile solvent. After concentration by evaporation of the fractions and recrystallization of the substance from ethyl acetate, 6.9 g of 1-methyl-androsta-1,4-diene-3,17-dione (69% of theory over 2 stages relative to 1α-methyl-androst-4-ene-3,17-dione in example 7) of melting point 168°-169° C. is obtained.

EXAMPLE 9

2-Iodo-androst-4-ene-3,17-dione 2.79 g (11 mmol) of iodine is added to 2.86 g (10 mmol) of androst-4-ene-3,17-dione and 0.875 g (11 mmol) of CuO in 30 ml of glacial acetic acid with stirring at room temperature. The reaction mixture is stirred under nitrogen atmosphere for 24 hours at 60° C. Under reduced pressure, acetic acid is distilled off and the residue is mixed with 50 ml of water. The water phase is extracted 3 times with 50 ml of ethyl acetate each, the combined ethyl acetate phases are washed with sodium thiosulfate solution and dried on sodium sulfate. After concentration by evaporation of the solution, 4.5 g of crude product is obtained. After recrystallization from ethyl acetate, 2.9 g of 2-iodo-androst-4-ene-3,17-dione (70% of theory) of melting point 92° C. is obtained.

EXAMPLE 10

Androsta-1,4-diene-3,17-dione 412 mg (1 mmol) of 2-iodo-androst-4-ene-3,17-dione of example 9 and 148 mg (2 mmol) of anhydrous lithium carbonate are stirred in 2 ml of dimethylformamide for 1 hour at 120° C. under nitrogen atmosphere. After cooling, it is added to water and extracted with ethyl acetate. The ethyl acetate solution is dried on sodium sulfate and then concentrated by evaporation. The residue is chromatographed on silica gel with ethyl acetate/hexane as mobile solvent. After concentration by evaporation of the fractions, 227 mg (80% of theory) of androsta-1,4-diene-3,17-dione of melting point 138°-139° C. is obtained.

EXAMPLE 11

17β-Acetoxy-2-iodo-1α-methyl-androst-4-en-3-one 6.88 g (20 mmol) of 17β-acetoxy-1α-methyl-androst-4-en-3-one and 1.75 g (22 mmol) of CuO in 60 ml of acetic acid are mixed with stirring at room temperature with 5.58 g (22 mmol) of iodine and stirred under nitrogen atmosphere for 24 hours at 60° C. Under reduced pressure, the acetic acid is largely distilled off and the residue is taken up in 100 ml of water. The water phase is extracted 3 times with 100 ml of ethyl acetate each. The ethyl acetate phases are washed with sodium thiosulfate solution and dried on sodium sulfate. After concentration by evaporation of the solution, 10 g of crude product is obtained. Recrystallization from ethyl acetate yields 8.8 g of 17β-acetoxy-2-iodo-1α-methyl-androst-4-en-3-one (93% of theory) of melting point 102° C.

Example 12

17β-Acetoxy-1-methyl-androsta-1,4-dien-3-one 1.4 g (3 mmol) of 17α-acetoxy-2-iodo-1α-methyl-androst-4-en-3-one of example 11 and 0.443 g (6 mmol) of anhydrous lithium carbonate are stirred in 6 ml of dimethylformamide for 1 hour at 120° C. under nitrogen atmosphere. After cooling, it is added to water and extracted with ethyl acetate. The ethyl acetate solution is dried on sodium sulfate and then concentrated by evaporation. The residue is chromatographed on silica gel with ethyl acetate/hexane as mobile solvent. After concentration by evaporation of the fractions, 0.95 g (92% of theory) of 17β-acetoxy-1-methyl-androsta-1,4-dien-3-one of melting point 173° C. is obtained.

EXAMPLE 13

2-Iodo-19-nor-androst-4-ene-3,17-dione 2.79 g (11 mmol) of iodine is added to 2.72 g (10 mmol) of 19-nor-androst-4-ene-3,17-dione and 0.875 g (11 mmol) of CuO in 30 ml of glacial acetic acid with stirring at room temperature. The reaction is stirred under nitrogen atmosphere for 24 hours at 60° C. Under reduced pressure, acetic acid is distilled off and the residue is mixed with 50 ml of water. The water phase is extracted 3 times with 50 ml of ethyl acetate, the combined ethyl acetate phases are washed with sodium thiosulfate solution and dried on sodium sulfate. After concentration by evaporation of the solution, 6.0 g of crude product is obtained. Chromatography of the crude product on silica gel with ethyl acetate/hexane as mobile solvent and recrystallization from ethyl acetate yields 2.9 g of 2-iodo-19-nor-androst-4-ene-3,17-dione (70% of theory) of melting point 108° C.

EXAMPLE 14

Estrone (1,3,5-estratrien-3-ol-17-one)

398 mg (1 mmol) of 2-iodo-19-nor-androst-4-ene-3,17-dione of example 13 and 148 mg (2 mmol) of anhydrous lithium carbonate are stirred in 2 ml of dimethylformamide for 2 hours at 120° C. under nitrogen atmosphere. After cooling, it is added to water, acidified with 2 n HCl to pH 3 and the product is extracted with ethyl acetate. The ethyl acetate solution is dried on sodium sulfate and then concentrated by evaporation. The residue is chromatographed on silica gel with ethyl acetate/hexane as mobile solvent. After concentration by evaporation of the fractions and recrystallization from ethyl acetate, 207 mg of estrone (1,3,5-estratrien-3-ol-17-one) (76% of theory) of melting point 258°-260° C. is obtained.

EXAMPLE 15

17β-Acetoxy-2-iodo-androst-4-en-3-one 2.79 g (11 mmol) of iodine is added to 3.28 g (10 mmol) of 17-acetoxy-androst-4-en-3-one and 0.875 g (11 mmol) of CuO in 30 ml of glacial acetic acid with stirring at room temperature. The reaction solution is stirred under nitrogen atmosphere for 24 hours at 60° C. Under reduced pressure, acetic acid is distilled off, and the residue is taken up in 50 ml of water. The water phase is extracted 3 times with 50 ml of ethyl acetate each, the ethyl acetate phases are washed with sodium thiosulfate solution and dried on sodium sulfate. Concentration by evaporation of the solution yields 4.5 g of crude product. After recrystallization from ethyl acetate, 2.85 g of 17β-acetoxy-2-iodo-androst-4-en-3-one (65% of theory) of melting point 92° C. is obtained.

EXAMPLE 16

17β-Acetoxy-androsta-1,4-dien-3-one 440 mg (1 mmol) of 17β-acetoxy-2-iodo-androst-4-en-3-one of example 15 and 148 mg (2 mmol) of anhydrous lithium carbonate are stirred in 2 ml of dimethylformamide for 1 hour at 130° C. under nitrogen atmosphere. After cooling, it is added to water and extracted with ethyl acetate. The ethyl acetate solution is dried on sodium sulfate and then concentrated by evaporation. The residue is chromatographed on silica gel with ethyl acetate/hexane as mobile solvent. After concentration by evaporation of the fractions, 0.3 g (91% of theory) of 17β-acetoxy-androsta-1,4-diene-3-dione of melting point 165° C. is obtained.

We claim:

1. A process for introducing a $\Delta^1$ double bond in a steroid skeleton compound simultaneously having a $\Delta^4$ double bond and at least one saturated carbonyl group, wherein a compound of formula I

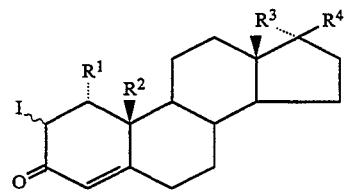

in which
R$^1$ stands for a hydrogen atom or a straight-chain or branched alkyl group with 1 to 4 carbon atoms,
R$^2$ stands for a hydrogen atom or a methyl group,
R$^3$ stands for a hydrogen atom,
R$^4$ stands for an acyloxy group with 1 to 4 carbon atoms in the acyl radical or
R$^3$ and R$^4$ together stand for a keto-oxygen atom, is dehydrohalogenated with a base in an amidic solvent at elevated temperature.

2. The process of claim 1, wherein the compound of formula I is dehydrohalogenated with magnesium oxide, lithium, sodium or potassium carbonate as the base.

3. The process of claim 1, wherein the compound of formula I is dehydrohalogenated in dimethylformamide or N-methyl-pyrrolidone as the solvent.

4. The process of claim 1, wherein the compound of formula I is dehydrohalogenated at a temperature of 100° to 150° C.

5. The process of claim 1, wherein 2α- or 2β-iodo-1α-methyl-androst-4-ene-3,17dione or a mixture of these isomers is dehydrohalogenated to Atamestan (1-methylandrosta-1,4-diene-3,17-dione).

6. The process of claim 1, wherein 2-iodo-19-norandrost-4-ene-3,17-dione is dehydrohalogenated to estrone (1,3,5-estratrien-3-ol-17-one).

7. The process of claim 1, wherein the dehydrohalogenation results in a compound of formula II

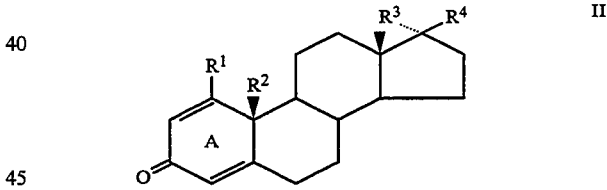

in which R$^1$, R$^2$, R$^3$ and R$^4$ have the meaning indicated in formula I.

8. The process of claim 7, wherein R$^2$ stands for a hydrogen atom, and, after the dehydrohalogenation, the A-ring of the compound aromatizes with the formation of a compound of formula II'

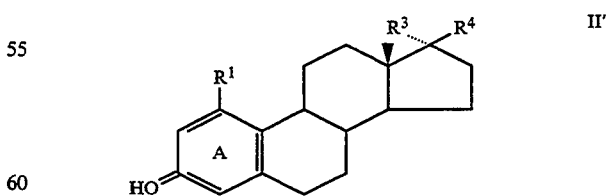

in which R$^1$, R$^3$ and R$^4$ have he meaning as indicated in formula I.

9. The process of claim 1, wherein the dehydrohalogenation produces a product containing less than 1% of the by-product having double bond in the $\Delta^4$ and $\Delta^6$ positions.